United States Patent
Decre et al.

(10) Patent No.: US 10,524,681 B2
(45) Date of Patent: Jan. 7, 2020

(54) LEAD AND A SYSTEM FOR MEDICAL APPLICATIONS

(71) Applicant: Medtronic Bakken Research Center B.V., Maastricht (NL)

(72) Inventors: Michel Marcel Jose Decre, Eindhoven (NL); Egbertus Reinier Jacobs, Overloon (NL); Johannes Wilhelmus Weekamp, Beek en Donk (NL); Marcus Franciscus Donker, Wijchen (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 1079 days.

(21) Appl. No.: 14/951,304

(22) Filed: Nov. 24, 2015

(65) Prior Publication Data
US 2016/0143555 A1 May 26, 2016

Related U.S. Application Data

(60) Provisional application No. 62/084,335, filed on Nov. 25, 2014.

(51) Int. Cl.
*A61N 1/05* (2006.01)
*A61B 5/0478* (2006.01)
*A61B 5/00* (2006.01)

(52) U.S. Cl.
CPC ............ *A61B 5/0478* (2013.01); *A61B 5/686* (2013.01); *A61N 1/0534* (2013.01)

(58) Field of Classification Search
CPC ..... A61B 5/0478; A61B 5/686; A61B 5/6868; A61N 1/0534; A61N 1/0529; A61N 1/3605
See application file for complete search history.

(56) References Cited

U.S. PATENT DOCUMENTS

| 6,024,702 A | 2/2000 | Iversen |
| 6,757,970 B1 | 7/2004 | Kuzma et al. |

(Continued)

FOREIGN PATENT DOCUMENTS

| EP | 2653187 A1 | 10/2013 |
| EP | 2656875 A1 | 10/2013 |

(Continued)

OTHER PUBLICATIONS

U.S. Appl. No. 14/951,237, filed by Decre, Michel Marcel Jose, on Nov. 24, 2015.

(Continued)

*Primary Examiner* — Lee S Cohen
*Assistant Examiner* — Erin M Cardinal
(74) *Attorney, Agent, or Firm* — Shumaker & Sieffert, P.A.

(57) ABSTRACT

In one example, a medical device system for at least one of delivery of electrical stimulation pulses or sensing of physiological signals, the system including an elongated carrier; and a thin film wound around the elongated carrier, wherein the thin film includes a plurality of electrical contacts, a plurality of electrodes located distal to the plurality of electrical contacts, and a plurality of conducting tracks, each of the plurality of conducting tracks providing an electrical connection between at least one of the plurality of electrodes and one of the plurality of electrical contacts, and wherein the thin film is wound around the elongated carrier from the distal end of the elongated film to the proximal end of the elongated thin film.

22 Claims, 11 Drawing Sheets

(56) References Cited

U.S. PATENT DOCUMENTS

| | | | |
|---|---|---|---|
| 6,939,338 B2 | 9/2005 | Waldhauser et al. | |
| 7,941,202 B2 | 5/2011 | Hetke et al. | |
| 8,494,641 B2 | 7/2013 | Boling et al. | |
| 8,565,894 B2 | 10/2013 | Vetter et al. | |
| 8,788,064 B2 | 7/2014 | Mercanzini et al. | |
| 2005/0033136 A1* | 2/2005 | Govari | A61B 5/0422 600/374 |
| 2005/0222658 A1* | 10/2005 | Hoegh | A61N 1/0534 607/116 |
| 2006/0030774 A1* | 2/2006 | Gray | A61N 1/37 600/435 |
| 2006/0206185 A1* | 9/2006 | Schuller | A61N 1/05 607/137 |
| 2006/0229686 A1* | 10/2006 | Giftakis | A61B 5/6864 607/45 |
| 2007/0027514 A1* | 2/2007 | Gerber | A61N 1/05 607/116 |
| 2007/0219551 A1* | 9/2007 | Honour | A61B 5/0422 606/41 |
| 2008/0140152 A1* | 6/2008 | Imran | A61N 1/0553 607/46 |
| 2009/0248122 A1* | 10/2009 | Pianca | A61N 1/0551 607/115 |
| 2011/0093052 A1 | 4/2011 | Anderson et al. | |
| 2011/0224765 A1* | 9/2011 | Harberts | A61N 1/0534 607/116 |
| 2011/0301665 A1* | 12/2011 | Mercanzini | A61N 1/0531 607/45 |
| 2012/0136420 A1* | 5/2012 | Pardoel | A61N 1/0534 607/116 |
| 2012/0310258 A1* | 12/2012 | Llinas | A61N 1/0541 606/130 |
| 2013/0204318 A1* | 8/2013 | Young | A61N 1/0534 607/45 |
| 2013/0238074 A1 | 9/2013 | Zimmerling | |
| 2013/0245733 A1 | 9/2013 | Yomtov | |
| 2013/0282090 A1* | 10/2013 | Decre | A61N 1/0551 607/116 |
| 2014/0128937 A1* | 5/2014 | Decre | A61N 1/3606 607/45 |
| 2014/0172058 A1* | 6/2014 | Elahi | A61N 1/05 607/116 |
| 2014/0194963 A1 | 7/2014 | Desai et al. | |
| 2014/0322964 A1 | 10/2014 | Deininger et al. | |
| 2016/0059004 A1* | 3/2016 | Mercanzini | A61N 1/0534 607/116 |

FOREIGN PATENT DOCUMENTS

| | | |
|---|---|---|
| EP | 2656876 A1 | 10/2013 |
| EP | 2742969 A1 | 6/2014 |
| WO | 2002089909 A1 | 11/2002 |
| WO | 2010055453 A1 | 5/2010 |

OTHER PUBLICATIONS

U.S. Appl. No. 14/950,549, filed by Young, Edward Willem Albert, on Nov. 24, 2015.

* cited by examiner

LEAD AND A SYSTEM FOR MEDICAL APPLICATIONS

This application claims the benefit of U.S. Provisional Application Ser. No. 62/084,335, by Jacobs et al., and filed Nov. 25, 2014, which is incorporated herein by reference in its entirety.

TECHNICAL FIELD

This disclosure relates, in some examples, to medical leads and medical device systems.

BACKGROUND

Implantable neurostimulation devices may treat acute or chronic neurological conditions. Deep brain stimulation (DBS), which may include, e.g., the mild electrical stimulation of cortical and/or sub-cortical structures, belongs to this category of implantable devices, and has been shown to be therapeutically effective for such conditions as Parkinson's disease, Dystonia, Epilepsy, Alzheimer's Disease, and Tremor. As another example, DBS may be used to treat psychiatric disorders (obsessive-compulsive disorder, depression). DBS systems generally include one or more leads connected to an implantable pulse generator.

SUMMARY

This disclosure is directed to, in some examples, medical leads including thin films incorporating both the electrodes of the medical leads and the conducting tracks for the medical leads. A lead for medical applications may include an elongated carrier and an elongated thin film wound around the elongated carrier, wherein the ends of the thin film may be both attached to the elongated carrier. The lead may be especially a lead for neurostimulation and sensing, such as a lead for DBS, which is implanted in to brain tissue to simulate regions of the brain.

In some examples, a distal end and a proximal end of the thin film are both attached to an elongated carrier. In the same or different examples, the thin film may have a substantially consistent width over its length, such as at the distal end including a plurality of electrodes, at its proximal end including plurality of electrical contacts and/or along an entire length of the thin film from the distal end to the proximal end.

In one example, this disclosure is directed to a medical device system for at least one of delivery of electrical stimulation pulses or sensing of physiological signals, the system comprising an elongated carrier; and a thin film wound around the elongated carrier, wherein the thin film includes a plurality of electrical contacts, a plurality of electrodes located distal to the plurality of electrical contacts, and a plurality of conducting tracks, each of the plurality of conducting tracks providing an electrical connection between at least one of the plurality of electrodes and one of the plurality of electrical contacts, and wherein the thin film is wound around the elongated carrier from the distal end of the elongated film to the proximal end of the elongated thin film.

In another example, this disclosure is directed to a method of manufacturing a medical device system comprising winding an elongated thin film around an elongated carrier in a helical fashion, wherein the thin film includes a plurality of electrical contacts, a plurality of electrodes located distal to the plurality of electrical contacts, and a plurality of conducting tracks, each of the plurality of conducting tracks providing an electrical connection between at least one of the plurality of electrodes and one of the plurality of electrical contacts, and wherein the thin film is wound around the elongated carrier from the distal end of the elongated film to the proximal end of the elongated thin film.

In a further example, this disclosure is directed to a medical device system comprising an implantable medical device including a first substantially sealed housing; an active lead can including a second substantially sealed housing operatively coupled to the implantable medical device; and a medical lead extending from the active lead can and operatively coupled to the active lead can, wherein the medical lead includes an elongated carrier; and a thin film wound around the elongated carrier, wherein the thin film includes a plurality of electrical contacts, a plurality of electrodes located distal to the plurality of electrical contacts, and a plurality of conducting tracks, each of the plurality of conducting tracks providing an electrical connection between at least one of the plurality of electrodes and one of the plurality of electrical contacts, and wherein the thin film is wound around the elongated carrier from the distal end of the elongated film to the proximal end of the elongated thin film.

The details of one or more examples of this disclosure may be set forth in the accompanying drawings and the description below. Other features, objects, and advantages of this disclosure may be apparent from the description and drawings, and from the claims.

DETAILED DESCRIPTION

In some examples, this disclosure is directed to medical leads, and systems including such leads, where the leads may include thin films incorporating both the electrodes of the medical leads and the conducting tracks for the medical leads. In some examples, a distal end and a proximal end of the thin film are both attached to an elongated carrier, e.g., by winding the thin film around the elongated carrier and/or attaching the thin film to the elongated carrier via an adhesive. In the same or different examples, the thin film may have a substantially consistent width over its length (from the distal end to proximal end), such as at the distal end including a plurality of electrodes, at its proximal end including a plurality of electrical contacts and/or along an entire length of the thin film from the distal end to the proximal end. In other examples, the width of the thin film may vary over its length This disclosure includes techniques for electrically and mechanically connecting a probe including electrodes and other components of a medical system configured to deliver therapy and/or provide sensing via the electrodes. For neural stimulation electrode arrays positioned inside the brain, a probe may include a flexible tube supporting a thin film containing electrodes and conducting tracks wrapped around the flexible tube. Examples of this disclosure may be applied to, for example, leads for deep brain stimulation, cochlear implants, hearing aids, pacemakers, implantable cardiac defibrillators, and other implantable systems including stimulation and/or sensing leads connected to a control box.

In a further example, a medical lead may connect to an active lead can (ALC). The ALC may contain at least a part of the electronics of the medical lead with the electronics being connected to the thin film in the area of the fixation zone. In particular, the ALC may be hermetically or substantially hermetically sealed and may include connections to address the plurality of electrodes on the distal end of the thin film, which is arranged at the distal end and next to the distal tip of the lead. The plurality of electrodes may comprise, for example, more than ten electrodes, more than twenty electrodes, such as approximately 40 electrodes. The electrodes may be arranged, in some examples, such that the electrodes are evenly distributed over the distal end of the lead.

Figure 1:
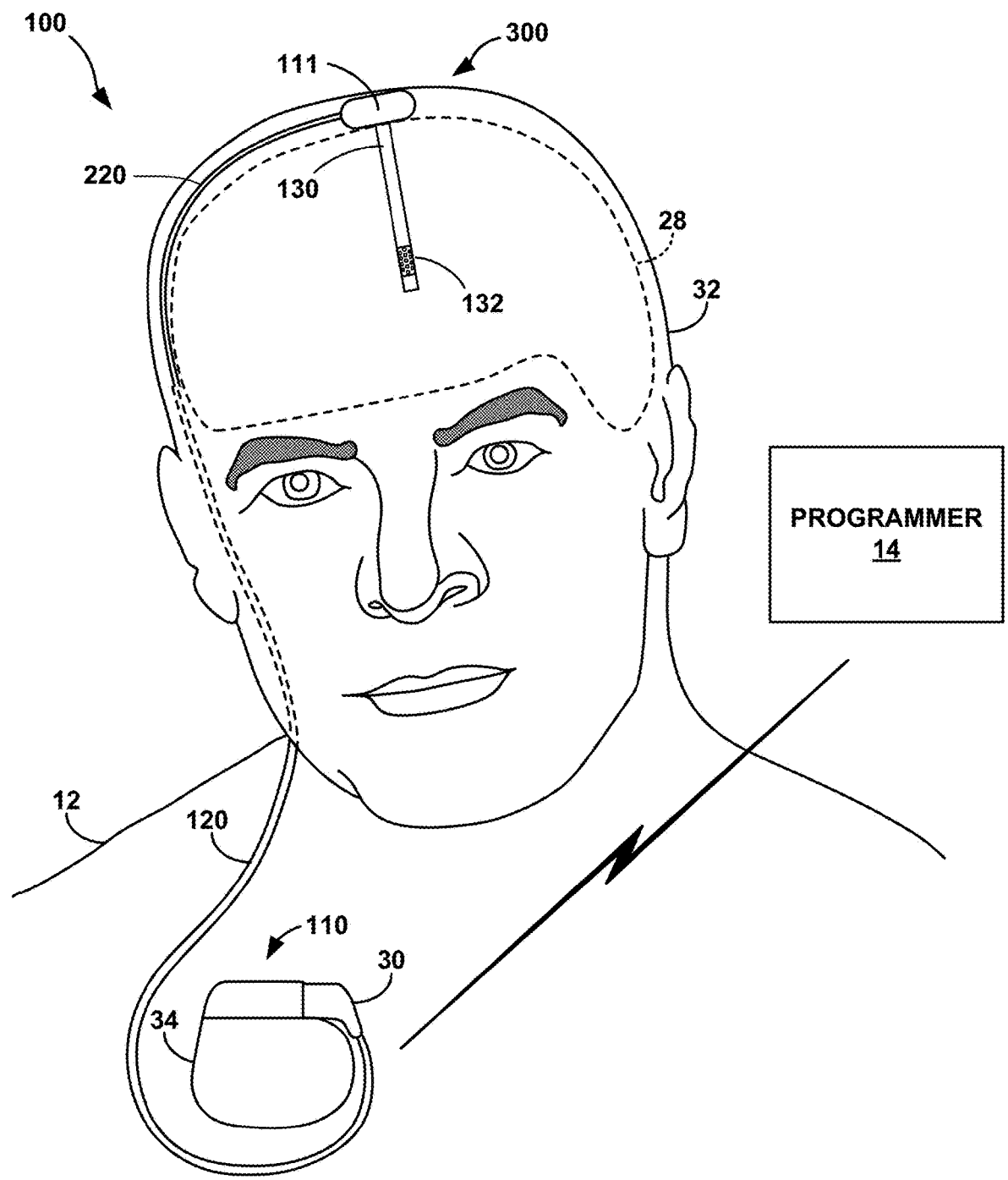
FIG. 1 is a conceptual diagram illustrating an example deep brain stimulation (DBS) system configured to sense a bioelectrical brain signal and deliver electrical stimulation therapy to a tissue site within a brain of a patient.

FIG. 1 is a conceptual diagram illustrating an example therapy system 100 that is configured to deliver therapy to patient 12 to manage a disorder of patient 12. Patient 12 ordinarily will be a human patient. In some cases, however, therapy system 100 may be applied to other mammalian or non-mammalian non-human patients. In the example shown in FIG. 1, therapy system 100 includes medical device programmer 14, IPG 110 (also referred to as an implantable medical device (IMD)), ALC 111, which connects to IPG 110 via lead extension 120 and lead 220. For example, the proximal end of lead extension 120 may be coupled to IPG 110 and at its distal end to the proximal end of lead 220 via an electrical connector(s) (not shown). Alternatively, a single lead may extend from IPG 110 to ALC 111. The distal end of lead 220 may be coupled to ALC 111 which is coupled to probe 130 with electrodes 132. IPG 110 may include at least one, such as two, stimulation generators configured to generate and deliver electrical stimulation therapy to one or more regions of brain 28 of patient 12 via one or more electrodes 132 of probe 130, respectively, alone or in combination with an electrode provided by outer housing 34 of IPG 110 and/or an electrode provided by the housing of ALC 111. In another example, any number of additional stimulation generators may be provided. Outer housing 34 of IPG 110 the housing of ALC 111 may each represent substantially sealed, such as hermetically sealed, housings containing electronics.

In the example shown in FIG. 1, therapy system 100 may be referred to as a DBS system because IPG 110 is configured to deliver electrical stimulation therapy directly to tissue within brain 28, for example, a tissue site under the dura mater of brain 28 or one or more branches or nodes, or a confluence of fiber tracks. In other examples, probe 130 may be positioned to deliver therapy to a surface of brain 28 (e.g., the cortical surface of brain 28). For example, in some examples, IPG 110 may provide cortical stimulation therapy to patient 12, for example, by delivering electrical stimulation to one or more tissue sites in the cortex of brain 28. Frequency bands of therapeutic interest in cortical stimulation therapy may include the theta band, and the gamma band.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive-compulsive disorder (OCD), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

DBS leads may implement monopolar, bipolar, or even tripolar stimulation. Neurostimulator devices with steering brain stimulation capabilities may have a large number M of electrode contacts, such as M>10, M>20 and/or M=40, that may be connected to electrical circuits such as current sources and/or (system) ground. Even more electrodes may be provided in some examples. Stimulation may be considered monopolar when the distance between the anode and cathode is several times larger than the distance of the cathode to the stimulation target. During monopolar stimulation in homogeneous tissue, the electric field may be distributed roughly spherically similar to the field from a point source. When the anode is located close to the cathode, creating a bipolar electrode combination, the distribution of the field becomes more directed in the anode-cathode direction. As a result, the field gets stronger and neurons may be more likely to be activated in this area due to a higher field gradient.

Polarization (de- and/or hyperpolarization) of neural tissue may play a prominent role for suppression of clinical symptoms, as well as induction of stimulation-induced side effects. In order to activate a neuron, the neuron has to be depolarized. Neurons may be depolarized more easily close to the cathode than by the anode (about 3-7 times more depending on type of neuron, etc.).

As illustrated, neurostimulation system 100 includes DBS probe 130 for brain applications with stimulation and/or recording electrodes 132, which may include, more than ten, more than twenty, or, for example, forty electrodes 132 provided on an outer body surface at the distal end of DBS probe 130. However, the techniques described in this disclosure are not so limited. As referred to herein, the distal end of a medical lead or probe may be the remote end of the lead with regard to the body surface area. In particular, in case of a lead for brain applications, the distal end of the lead is the lower end of the lead, that is inserted deeper into the brain tissues, and which is remote to the burr-hole of the skull, through which the lead is implanted.

IPG 110 may include more than one implantable pulse generator for delivery of neurostimulation via electrodes 132, and/or one or more sensors configured to sense electrical fields within the brain of the patient, such as electrical fields representing a patient's brain activity and/or electrical fields created by delivery of DBS therapy. In examples in which IPG 110 includes both an implantable pulse generator and one or more sensors, in various examples, either the same set of electrodes or different sets of electrodes may be used for sensing as those used for delivery of DBS therapy.

In the example shown in FIG. 1, IPG 110 may be implanted within a subcutaneous pocket in the pectoral region of patient 12. IPG 110 may be surgically implanted in the chest region of a patient, such as below the clavicle or in the abdominal region of a patient. In other examples, IPG 110 may be implanted within other regions of patient 12, such as a subcutaneous pocket in the abdomen or buttocks of patient 12 or proximate to the cranium of patient 12. The neurostimulation system 100 may further include a lead extension 120 connected to IPG 110 and running subcutaneously to the skull, such as along the neck, where it terminates in a distal end that couples to a proximal end of lead 220 via one or more connectors. The proximal end of lead 220 extends from the connector to ALC 111, which in turn, couples to DBS probe 130. DBS probe 130 may be implanted in the brain tissue, for example, through a burr-hole in the skull. In some examples, ALC 111 may be located adjacent the burr-hole and external to the skull and beneath the skin. In other examples, ALC 111 may be located into a surgeon-created recess adjacent the burr-hole in the skull and/or into the burr hole itself.

Implanted lead extension 120 is coupled at one end to IPG 110 via connector block 30 (also referred to as a header), which may include, for example, electrical contacts that electrically couple to respective electrical contacts on lead extension 120. In turn, conductors of lead extension 120 are electrically coupled to the proximal end of lead 220, as set forth above. Lead 220 extends to, and comprises, the ALC 111. ALC 111 includes electronic module 500 with an active switch matrix to direct stimulation from IPG 110 to any combination of electrodes 132. Likewise, the active switch matrix electronic module 500 can direct sensing signals from any combination of electrodes 132 to IPG 110. In some examples, ALC 111 may digitize sensing signals prior to sending them to IPG 110. IPG 110 may store the sensing signals or a subset of the sensing signals, analyze the sensing signals or a subset of the sensing signals, and/or forward the sensing signals or a subset of the sensing signals to an external device via a wireless transmission.

Lead extension 120 traverses from the implant site of IPG 110, along the neck of patient 12. The distal end of lead extension 120 may connect to a proximal end of lead 220, e.g., somewhere along the cranium of patient 12. The lead extends to ALC 111 to access brain 28. IPG 110 and ALC 111 can be constructed of biocompatible materials that resist corrosion and degradation from bodily fluids. IPG 110 may comprise a hermetic outer housing 34 to substantially enclose components, such as a processor, a therapy module, and memory. Likewise, ALC 111 may comprise a hermetic outer housing to substantially enclose electronic components.

In the example shown in FIG. 1, probe 130 is implanted within brain 28 in order to deliver electrical stimulation to one or more regions of brain 28, which may be selected based on many factors, such as the type of patient condition for which therapy system 100 is implemented to manage. Other implant sites for probe 130 and IPG 110 are contemplated. For example, IPG 110 may be implanted on or within cranium 32. As another example, probe 130 may be implanted within the same hemisphere as that shown in FIG. 1 but at multiple other target tissue sites or IPG 110 may be coupled to one or more medical leads that are implanted in one or both hemispheres of brain 28.

During implantation of probe 130 within patient 12, a clinician may attempt to position electrodes 132 of probe 130 such that electrodes 132 are able to deliver electrical stimulation to one or more target tissue sites within brain 28 to manage patient symptoms associated with a disorder of patient 12. Probe 130 may be placed at any location within brain 28 such that electrodes 132 are capable of providing electrical stimulation to target therapy delivery sites within brain 28 during treatment.

The anatomical region within patient 12 that serves as the target tissue site for stimulation delivered by system 100 may be selected based on the patient condition. Different neurological or psychiatric disorders may be associated with activity in one or more of regions of brain 28, which may differ between patients. Accordingly, the target therapy delivery site for electrical stimulation therapy delivered by probe 130 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, probe 130 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, probe 130 may be implanted to deliver electrical stimulation to regions within the Circuit of Papez, such as, for example, one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

The techniques of this disclosure may be implemented in combination with systems including smaller electrodes, such as electrodes manufactured using thin film manufacturing. Examples of such manufacturing techniques for a medical lead made from a thin film based on thin film technology are disclosed in United States Patent Application Publication No. 2011/0224765, titled, "SPIRALED WIRES IN A DEEP-BRAIN STIMULATION PROBE," the entire contents of which are incorporated by reference herein. The thin film medical leads may be fixed on an elongated carrier to form a medical lead. These medical leads may include multiple electrode areas and may enhance the precision to address the appropriate target in the brain and relax the specification of positioning. Meanwhile, undesired side effects due to undesired stimulation of neighboring areas may be limited.

Although lead 220 and lead extension 120 are shown in FIG. 1, in other examples, probe 130 may be coupled to IPG 110 via a single lead that extends from ALC 111 to IPG 110. Moreover, although FIG. 1 illustrates system 100 as including a single probe 130 coupled to IPG 110 via lead 220, lead extension 120 and ALC 111, in some examples, system 100 may include two or more medical leads and ALCs. In some examples, each ALC may be associated with a single medical lead; in other examples, more than one medical lead may extend from an ALC. In some example, system 100 may include multiple DBS probes rather than a single DBS probe 130.

In the example shown in FIG. 1, electrodes 132 of probe 130 are shown as an array of electrodes with a complex electrode array geometry that is capable of producing shaped electrical fields. An example of a complex electrode array geometry may include an array of electrodes positioned at different axial positions along the length of a medical lead, as well as at different angular positions about the periphery, for example, circumference, of the medical lead. The complex electrode array geometry may include multiple electrodes (e.g., partial ring or segmented electrodes) around the perimeter of each medical lead 220. In other examples, the complex electrode array geometry may include electrode pads distributed axially and circumferentially about the medical lead 220. In either case, by having electrodes at different axial and angular positions, electrical stimulation may be directed in a specific direction from probe 130 to enhance therapy efficacy and reduce possible adverse side effects from stimulating a large volume of tissue. In some examples, the array of electrodes may be combined with one or more ring electrodes on probe 130.

In some examples, outer housing 34 of IPG 110 and/or the housing of ALC 111 may include one or more stimulation and/or sensing electrodes. For example, housing 34 can comprise an electrically conductive material that is exposed to tissue of patient 12 when IPG 110 is implanted in patient 12, or an electrode can be attached to housing 34.

IPG 110 and ALC 111 may deliver electrical stimulation therapy to brain 28 of patient 12 according to one or more therapy programs. A therapy program may define one or more electrical stimulation parameter values for therapy generated by a stimulation generator of IPG 110 and delivered from IPG 110 to a target therapy delivery site within patient 12 via one or more electrodes 132. The electrical stimulation parameters may define an aspect of the electrical stimulation therapy, and may include, for example, voltage or current amplitude of an electrical stimulation signal, a frequency of the electrical stimulation signal, and, in the case of electrical stimulation pulses, a pulse rate, a pulse width, a waveform shape, and other appropriate parameters such as duration or duty cycle. In addition, if different electrodes are available for delivery of stimulation, a therapy parameter of a therapy program may be further characterized by an electrode combination, which may define electrodes 132 selected for delivery of electrical stimulation and their respective polarities. In some examples, as an alternative to stimulation pulses, stimulation may be delivered using a continuous waveform and the stimulation parameters may define this waveform.

In addition to being configured to deliver therapy to manage a disorder of patient 12, therapy system 100 may be configured to sense bioelectrical brain signals of patient 12. For example, IPG 110 may include a sensing module that is configured to sense bioelectrical brain signals within one or more regions of brain 28 via a subset of electrodes 132, another set of electrodes, or both. Accordingly, in some examples, electrodes 132 may be used to deliver electrical stimulation from the therapy module to target sites within brain 28 as well as sense brain signals within brain 28. However, IPG 110 can also, or alternatively, use a separate set of sensing electrodes to sense the bioelectrical brain signals. In some examples, the sensing module of IPG 110 may sense bioelectrical brain signals via one or more of the electrodes 132 that are also used to deliver electrical stimulation to brain 28. In other examples, one or more of electrodes 132 may be used to sense bioelectrical brain signals while one or more different electrodes of electrodes 132 may be used to deliver electrical stimulation.

Examples of bioelectrical brain signals include, but are not limited to, electrical signals generated from local field potentials (LFPs) within one or more regions of brain 28, such as, but not limited to, an electroencephalogram (EEG) signal or an electrocorticogram (ECoG) signal. In some examples, the electrical signals within brain 28 may reflect changes in electrical current produced by the sum of electrical potential differences across brain tissue.

External medical device programmer 14 is configured to wirelessly communicate with IPG 110 as needed to provide or retrieve therapy information. Programmer 14 is an external computing device that the user, for example, the clinician and/or patient 12, may use to communicate with IPG 110. For example, programmer 14 may be a clinician programmer that the clinician uses to communicate with IPG 110 and program one or more therapy programs for IPG 110. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IPG 110.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, then the buttons may be dedicated to performing a certain function, for example, a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IPG 110.

When programmer 14 is configured for use by the clinician, programmer 14 may be used to transmit programming information to IPG 110. Programming information may include, for example, hardware information, such as the type of ALC 111, the type of probe 130, the arrangement of electrodes 132 on probe 130, the position of probe 130 within brain 28, one or more therapy programs defining therapy parameter values, and any other information that may be useful for programming into IPG 110. Programmer 14 may also be capable of completing functional tests (e.g., measuring the impedance of electrodes 132 of probe 130).

With the aid of programmer 14 or another computing device, a clinician may select one or more therapy programs for therapy system 100 and, in some examples, store the therapy programs within IPG 110. Programmer 14 may assist the clinician in the creation/identification of therapy programs by providing physiologically relevant information specific to patient 12.

Programmer 14 may also be configured for use by patient 12. When configured as a patient programmer, programmer 14 may have limited functionality (compared to a clinician programmer) in order to prevent patient 12 from altering critical functions of IPG 110 or applications that may be detrimental to patient 12.

Whether programmer 14 is configured for clinician or patient use, programmer 14 is configured to communicate with IPG 110 and, optionally, another computing device, via wireless communication. Programmer 14, for example, may communicate via wireless communication with IPG 110 using radio frequency (RF) telemetry techniques known in the art. Programmer 14 may also communicate with another programmer or computing device via a wired or wireless connection using any of a variety of local wireless communication techniques, such as RF communication according to the 802.11 or BLUETOOTH® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IPG 110 and another programmer via remote telemetry techniques known in the art, communicating via a local area network (LAN), wide area network (WAN), public switched telephone network (PSTN), or cellular telephone network, for example.

Therapy system 100 may be implemented to provide chronic stimulation therapy to patient 12 over the course of several months or years. However, system 100 may also be employed on a trial basis to evaluate therapy before committing to full implantation. If implemented temporarily, some components of system 100 may not be implanted within patient 12. For example, patient 12 may be fitted with an external medical device, such as a trial stimulator, rather than IPG 110. The external medical device may be coupled to percutaneous medical leads or to implanted medical leads via a percutaneous extension. If the trial stimulator indicates DBS system 100 provides effective treatment to patient 12, the clinician may implant a chronic stimulator within patient 12 for relatively long-term treatment.

Figure 2:
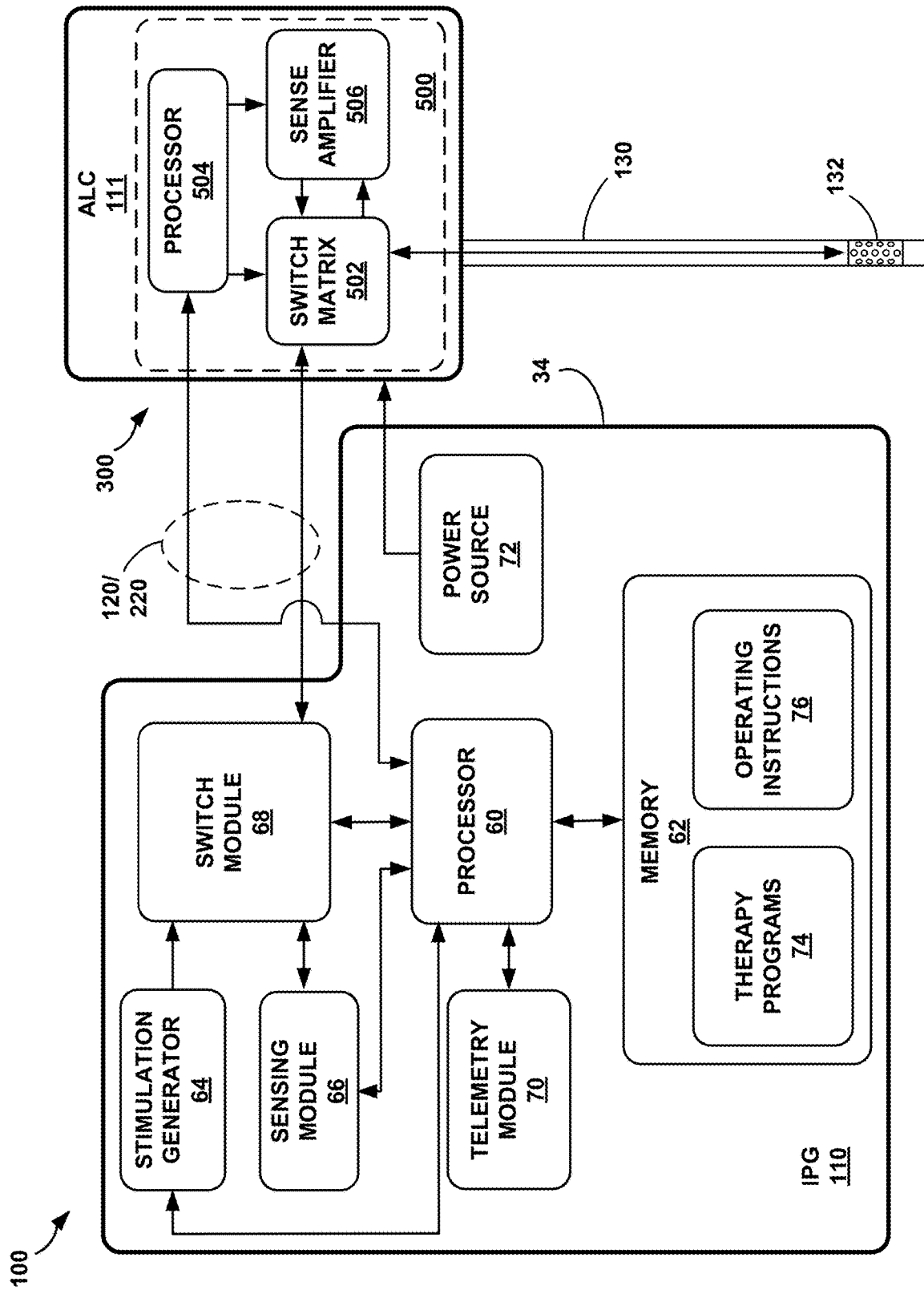
FIG. 2 is a functional block diagram illustrating components of an example medical device system including an implantable pulse generator and a separate active lead can (ALC) with a switch matrix to direct signals from the implantable pulse generator to different electrodes.

FIG. 2 is functional block diagram illustrating components of an example therapy system 100 including IPG 110 and ALC 111. In the example shown in FIG. 2, IPG 110 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IPG 110 to perform various functions described herein.

In the example shown in FIG. 2, memory 62 stores therapy programs 74 and operating instructions 76, for example, in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. The stimulation signals delivered by IPG 110 may be of any form, such as stimulation pulses, continuous-wave signals (e.g., sine waves), or the like. Operating instructions 76 guide general operation of IPG 110 under control of processor 60, and may include instructions for monitoring brain signals within one or more brain regions via electrodes 132 and delivering electrical stimulation therapy to patient 12.

Stimulation generator 64, under the control of processor 60, generates stimulation signals for delivery to patient 12 via selected combinations of electrodes 132. In some examples, stimulation generator 64 generates and delivers stimulation signals to one or more target regions of brain 28 (FIG. 1), via a select combination of electrodes 132, based on one or more stored therapy programs 74. Processor 60 selects the combination of electrodes 132 with control signals to processor 504 of ALC 111. In turn, processor 504 of ALC 111 selectively activates active switch matrix 504 to direct the stimulation signals received from stimulation generator 64 to the selected electrodes 132. The stimulation parameter values and target tissue sites within brain 28 for stimulation signals or other types of therapy may depend on the patient condition for which therapy system 100 is implemented to manage.

The processors described in this disclosure, including processor 60 and processor 504, may include one or more digital signal processors (DSPs), general-purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more therapy programs.

Processor 60 may control switch module 68 to select stimulation generator 64 or sensing module 66. In turn, processor 60 directs processor 504 of electronic module 500 to apply the stimulation signals generated by stimulation generator 64 to selected combinations of electrodes 132, or to sense signals from selected combinations of electrodes 132 via sense amplifier 506 of electronic module 500. In particular, active switch matrix 502 of electronic module 500 may couple stimulation signals to selected conducting tracks within probe 130, which, in turn, deliver the stimulation signals to selected electrodes 132. Hence, although there may be many, for example, 40, electrodes, active switch matrix 502 may select a subset of one, two or more electrodes for delivery of stimulation pulses. Active switch matrix 502 may be a switch array, an array of one or more transistors such as Field-Effect Transistors (FETs), switch matrix, multiplexer and/or demultiplexer, or any other type of switching module configured to selectively couple stimulation energy to selected electrodes 132 and to selectively sense bioelectrical brain signals with selected electrodes 132. Hence, stimulation generator 64 is coupled to electrodes 132 via switch module 68, conductors within cable 120 between IPG 110 and ALC 111, active switch matrix 502, and conducting tracks within probe 130. Additionally, the logic path between stimulation generator and electrodes 132 may include one or more discrete components such as capacitors, resistors, logic gates, transistors, and the like. Thus, it will be understood that when reference is made to coupling of stimulation generator 64 or other components of IPG 110 to electrodes 132, this refers to the enabling of a logic path between the logic components so that signals may be transferred there between, and is not intended to necessarily require a direct electrical coupling of the components.

In some examples, however, IPG 110 does not include switch module 68 and all switching functions may be performed by active switch matrix 502. For example, IPG 110 may include multiple sources of stimulation energy (e.g., current sources). Additionally or alternatively, a stimulation generator similar to stimulation generator 64 may reside within ALC (not shown) and may generate the stimulation pulses that are routed to electrodes 132 via active switch matrix 502. In such cases, the stimulation generator within the ALC may receive power from power source 72 and may receive control signals from stimulation generator 64 or other logic of IPG 110. The stimulation generator in ALC may be provided in addition to, or instead of, stimulation generator 64 of IPG 110. Thus, electronics for driving probe 130 and electrodes 132 of lead may reside in IPG 110, ALC 111, or some combination thereof. Stimulation generator 64 and/or a stimulation generator residing within ALC 111 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and active switch matrix 502 may be configured to deliver multiple channels of stimulation on a time-interleaved basis. For example, active switch matrix 502 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via active switch matrix 502, sense amplifier 506, and a selected subset of electrodes 132 or with one or more electrodes 132 and at least a portion of a conductive outer housing 34 of IPG 110, at least a portion of a conductive outer housing of ALC 111, an electrode on outer housing 34 of IPG 110, an electrode on an outer housing of ALC 111, or another reference. Processor 60 may control switch module 68 and/or switch matrix 502 to electrically connect sensing module 66 to selected electrodes 132 via active switch matrix 502 and sense amplifier 506 of ALC 111. In this way, sensing module 66 may selectively sense bioelectrical brain signals with different combinations of electrodes 132.

Telemetry module 70 is configured to support wireless communication between IPG 110 and an external programmer 14 or another computing device under the control of processor 60. Processor 60 of IPG 110 may receive, as updates to programs, values for various stimulation parameters from programmer 14 via telemetry module 70. The updates to the therapy programs may be stored within therapy programs 74 portion of memory 62. Telemetry module 70 in IPG 110, as well as telemetry modules in other devices and systems described herein, such as programmer 14, may accomplish communication by RF communication techniques. In addition, telemetry module 70 may communicate with external medical device programmer 14 via proximal inductive interaction of IPG 110 with programmer 14. Accordingly, telemetry module 70 may send and receive information to/from external programmer 14 on a continuous basis, at periodic intervals, or upon request from IPG 110 or programmer 14.

Power source 72 delivers operating power to various components of IPG 110. Power source 72 may include a small rechargeable or non-rechargeable battery and a power generation circuit to produce the operating power. Recharging may be accomplished through proximal inductive interaction between an external charger and an inductive charging coil within IPG 110. In some examples, power requirements may be small enough to allow IPG 110 to utilize patient motion and implement a kinetic energy-scavenging device to trickle charge a rechargeable battery. In other examples, traditional batteries may be used for a limited period of time.

Figure 3:
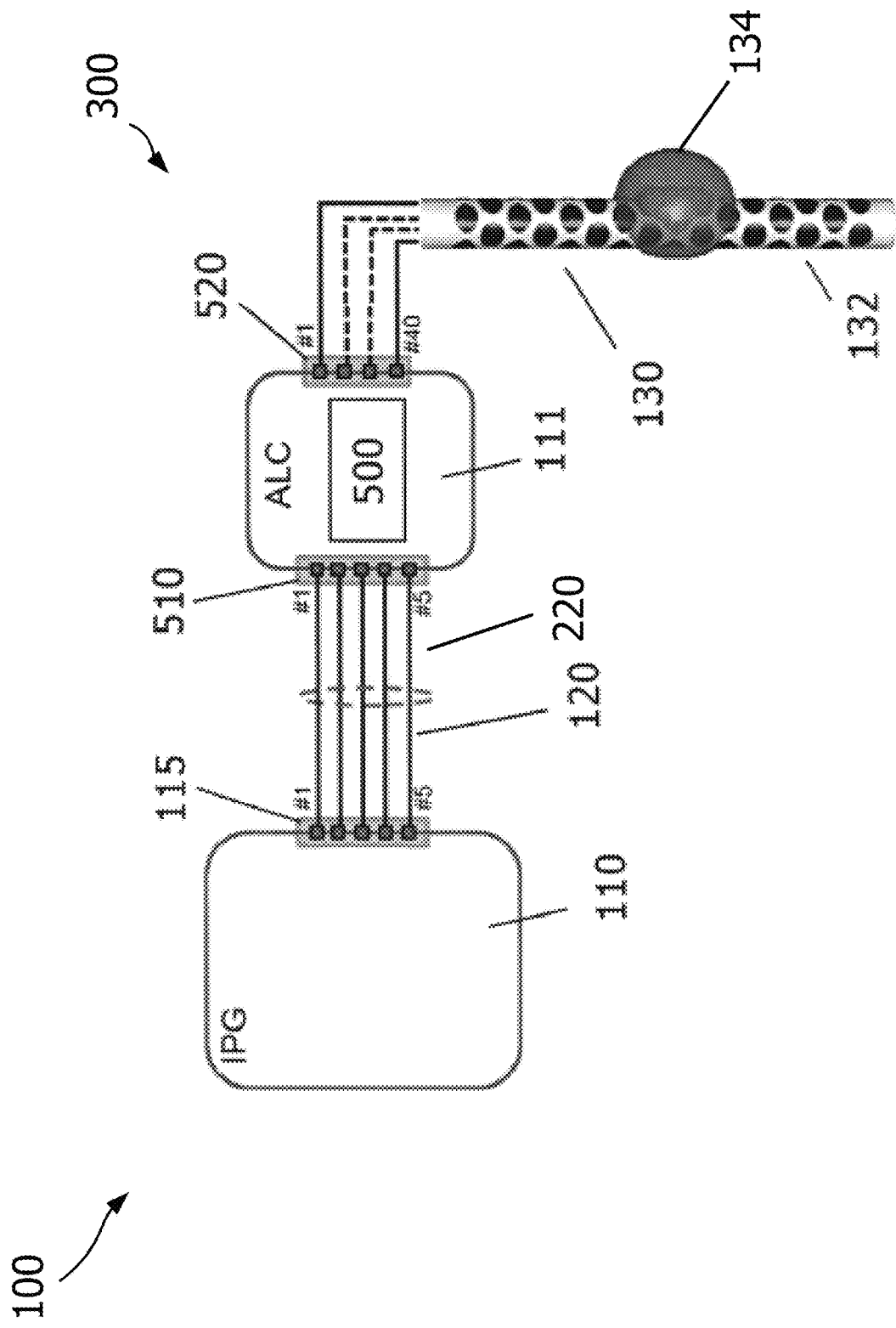
FIG. 3 illustrates the electrical paths between an implantable pulse generator and a separate ALC with a switch matrix to direct signals from the implantable pulse generator to different electrodes.

FIG. 3 is a functional block diagram illustrating electrical connections between IPG 110, ALC 111 and DBS probe 130 within neurostimulation system 100. As illustrated in FIG. 3, IPG 110 connects lead extension 120 via connectors 115. Connectors at the distal end of lead extension 120 may couple to connectors at the proximal end of lead 220. In one example, lead 300 comprises lead 220, ALC 111 and DBS probe 130. More specifically, a distal end of lead 220 may extend to ALC 111 which, in turn, may connect to DBS probe 130. DBS probe 130 may comprise a separate conductor for each of electrodes 132 which are routed via connector 520. ALC 111 includes electronic module 500 with an active switch matrix 502 (FIG. 2) to direct stimulation signals from IPG 110 to any combination of electrodes 132 and/or direct sensed signals from electrodes 132 to IPG 110.

In the illustration of FIG. 3, example stimulation/sensing zone 134 is depicted. Stimulation/sensing zone 134 utilizes a subset of electrodes 132 for stimulation or sensing. Active switch matrix 502 of electronic module 500 may be used to select any combination of electrodes for stimulation and sensing functionality. In some examples, active switch matrix 502 of electronic module 500 within ALC 111 can connect any number of the available electrodes to any number of one or more stimulation signals or ground such that stimulation is not limited to being provided across pairs of two of electrodes 132. In this manner, other stimulation and sensing zones may be activated using different subsets of electrodes and/or by using field steering techniques such as varying the resistance of paths in multi-electrode combinations, anodal shielding and other field steering techniques. As set forth above, the stimulation signals may be generated by voltage-controlled or current-controlled logic such a stimulation generator 64 that resides within IPG 110, within ALC, or a combination thereof.

In the example configuration of FIG. 3, lead extension 120/lead 220 and connectors 115, 510 provide five conductive paths between IPG 110 and ALC 111. IPG 110 has a N-pin connector 115 (e.g., N=5) which is connected via the lead extension 120 and lead 220 with the 5-pin connector 510 (or N-pin connector 510) of ALC 111. In the example of IPG 110 and ALC 111, the five conductors between IPG 110 and ALC 111 may include a power conductor, a ground conductor, a communication conductor, a conductor for a first pulse generator within IPG 110, and a conductor for a second pulse generator within IPG 110. The control line may provide instructions from IPG 110 for directing stimulation pulses to selected electrodes via active switch matrix 502 of electronic module 500 or providing sensing connectivity between electrodes and IPG 110 via active switch matrix 502 of electronic module 500. In some examples, the power conductor may serve a dual purpose of providing clock or timing information between IPG 110 and ALC 111. For example, the voltage over the power conductor may be sent as a square wave or other periodic signal. In some examples, the timing information provided by the power conductor may be used to coordinate sensing and stimulation functions as isolating sensing circuitry, such as sense amplifier 506 (FIG. 2) in ALC 111, from the stimulation generators may be required to protect the sensing circuitry from the stimulation pulse. Any number of conductors may be provided in the alternative, with the conductors serving similar or different functions to those set forth above.

Lead extension 120 may couple to a proximal end of lead 220 such that the five conductive paths of lead extension 120 are coupled to corresponding conductive paths provided by the proximal end of lead 220. The distal end of lead 220 extends to connector 510 of ALC 111. Connector 510 may be integrated within lead 220 such that ALC 111 is coupled to lead 220 is a permanent or semi-permanent manner. In other examples, connector 510 may allow for the proximal end of lead 220 to be selectively detached from connector 510.

ALC 111 may include a 5-pin feedthrough connector 510 which is configured to be coupled to the five conductive paths of lead 220. ALC 111 may also include a M-pin connector 520 (e.g., M=40) for DBS probe 130. It is mechanically possible to design these two feedthrough connectors 510, 520 with a high pin density to reduce the area of ALC 111 significantly. However, this area advantage may only materialize if the electrical components of ALC 111 are shrunk in similar proportions as the feedthrough connectors 510, 520. Moreover, a very thin ALC 111, most desirable to reduce its impact on skin erosion, may need a high pin density, but also a reduction in the height of both connectors 510, 520 and interior electrical components. Thus, both the electronics volume and area of ALC 111 are miniaturized to realize a small ALC 111. Note that techniques to shrink ALC 111 can also be applied to the IPG 110, or any other implant module, for example, to trade for an increase in battery life and/or increased functionality.

Figure 4A:
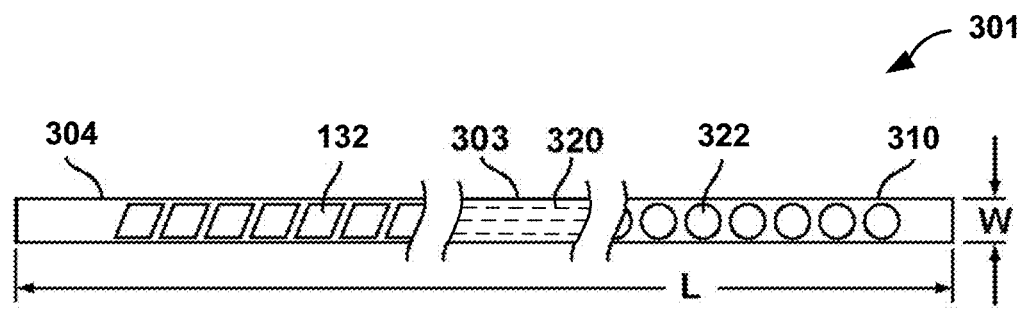
FIGS. 4A-4C illustrate components of a medical lead for stimulation and/or sensing that may be used in the systems of FIGS. 1-3.
Figure 4B:
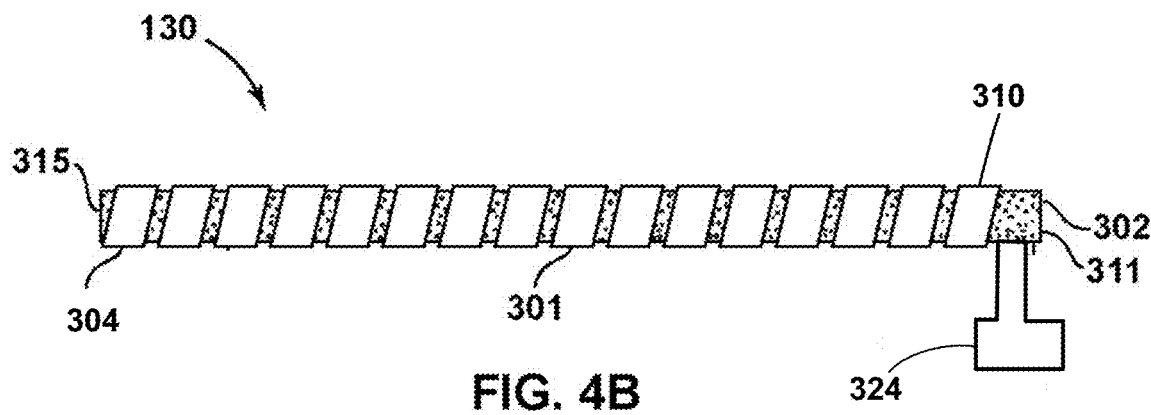
Figure 4C:
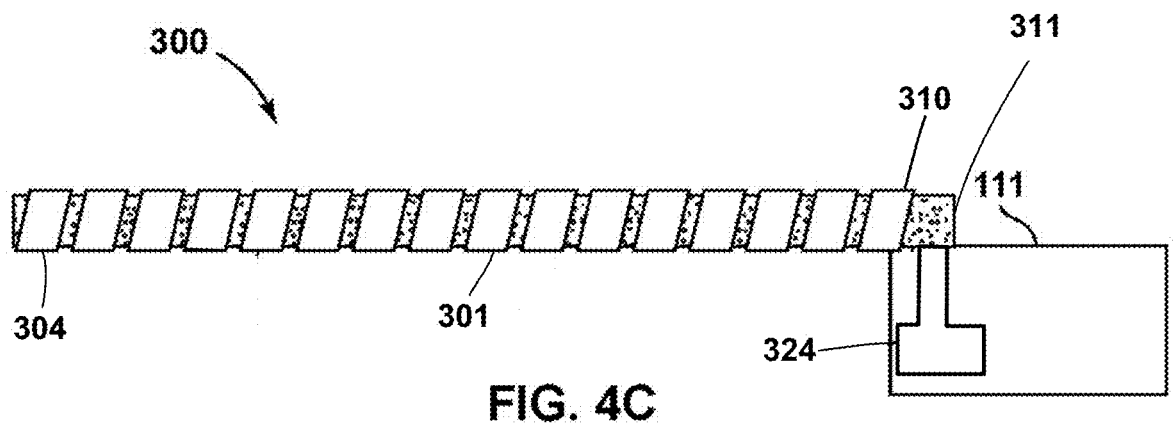

FIGS. 4A-4C illustrate components of an example medical lead for stimulation and/or sensing. FIG. 4A shows a conceptual illustration of thin film 301 that is used to manufacture lead 300. In FIG. 4A, thin film 301 is shown prior to being wound around elongated carrier 302 (e.g., as shown in FIG. 4B). As shown in FIG. 4A, thin film 301 may be a thin film strip having the substantially the same width 'W' over the whole length 'L'. As shown in FIG. 4B, thin film 301 may be wound around elongated carrier 302 from the distal end 304 of thin film 301 to the proximal end 310 of thin film 301, e.g., to attach or otherwise secure thin film 301 to elongated carrier 302. Thin film 301 having substantially the same width W may provide the possibility that a constant winding of thin film 301 can be made around the outer surface of elongated carrier 302 in a helical or coiled fashion. The winding process may be performed to facilitate tube flexibility without breaking thin film 301 and/or to provide MRI compatibility, which comes from the coiled configuration of the conductors of thin film 301 as wound on elongated carrier 302. As will be described further below, in some examples, thin film 301 may have substantially the same width in the portion between its distal end 304 and its proximal end 310 while in other examples, a distal portion and/or proximal portion of thin film 301 may have a greater width compared to the width of thin film 301 at other portions between distal end 304 and/or proximal end 310. Furthermore, such a design helps to keep the tension and stress within thin film 301, for example, during the winding process, but also during use, at an uncritical level. Consequently, the risk of damages and production losses is decreased. In some examples, the thin film strip may allow an improved winding around elongated carrier 302. Furthermore, the thin film strip may help automatize the manufacturing process and, in particular, an automatized winding process may be provided.

Lead 300, shown in FIG. 4C, includes ALC 111 and DBS probe 130 of a DBS system 100. DBS probe 130 comprises an elongated carrier 302 for thin film 301, said elongated carrier 302 providing the mechanical configuration of DBS probe 130 and thin film 301. Elongated carrier 302 may be a flexible elongated carrier, such as a flexible tubing. In some examples, elongated carrier 302 may be formed from a silicone tubing.

Elongated carrier 302 may have any suitable configuration. In some examples, elongated carrier 302 may be an elongated member having a circular cross-section, although other cross-sections are contemplated, such as, e.g., square or hexagonal. Elongated carrier 302 may be a solid member or have a hollow core. In some examples, it is preferred that elongated carrier 302 be relatively stiff during implantation but able to flex or bend to some degree after implantation. The hollow core may allow for the insertion of a stiffening member such as a stylet into the hollow core, e.g., during implantation of lead 300. Elongated carrier 302 may be configured to not substantially shrink, stretch, or compress during and/or after implantation.

In some examples, elongated carrier 302 should be flexible and have a good rotational torque transfer, e.g., in instances of permanent (chronic) implant of lead 300. Some acute applications may have a different set of preferences. For instance, in acute implantation, no burr-hole devise may be used and flexibility and limited compressibility are of less concern.

Elongated carrier 302 may be formed of any suitable material including silicone, titanium, and/or polyether ether ketone (PEEK) based materials. For the mechanical requirements as mentioned above, other polymers can be more useful e.g. bionate. In addition, metal tubes (e.g., laser machined to bendable chains) may be used. In acute applications, a solid metal may be used for elongated carrier 302. In acute application, there may not be a need for elongated carrier 302 to be hollow or flexible. In chronic applications, elongated carrier 302 is implanted with a stiffener inside. After implantation, the stiffener may be removed.

Distal portion of lead 300 may have a diameter between about 0.5 millimeters (mm) and about 3 mm diameter, e.g., about 1.3 mm. The diameter of lead 300 may be defined by the diameter of carrier core 302 in combination with the thickness of thin film 301 and any coating applied over carrier core 302 and/or thin film 301. The proximal portion of lead 300 (the portion adjacent to ALC 111) may have a diameter between about 0.5 mm and about 4 mm diameter. The length of lead 300 may be about 10 centimeters (cm) to about 20 cm, e.g., about 15 cm, and may vary based on the particular application, e.g., acute versus chronic implantation. Other dimensions than those examples described herein are contemplated.

Thin film 301 may include at least one electrically conductive layer, such as one made of a biocompatible material. Thin film 301 is assembled to elongated carrier 302 and further processed to constitute DBS probe 130. Thin film 301 for a medical lead may be formed by a thin film product having a distal end 304, a cable 303 with conducting tracks and a proximal end 310, as illustrated in FIG. 4A.

As shown, thin film 301 may include three sections, i.e., distal end 304 with electrodes 132, cable section 303 with conducting tracks 320, and proximal end 310 with proximal contacts 322. Only three individual conducting tracks 320 are shown in FIG. 4A for ease of illustration. However, cable section 303 may include an individual conducting track 320 corresponding to each individual electrode 132 and contact 322. The individual conducting tracks may be electrically isolated from each other. Each individual conducting track 320 electrically couples a respective distal electrode to a respective proximal contact 322. As already mentioned above, thin film 301 may be wrapped around an elongated carrier 302 so as to form a lead. Thus, for manufacturing of lead 300, elongated carrier 302 is provided. This elongated carrier 302 may be, for example, a flexible tube including a flexible medical grade polymer. Further, elongated thin film 301 is provided and wrapped around elongated carrier 302.

ALC 111 comprises the switch matrix of the DBS steering electronics. Distal end 304 comprises electrodes 132 (not shown in FIG. 4C) for the brain stimulation and/or sensing brain signals. Proximal end 310 comprises interconnect contacts 322 (not shown in FIG. 4C) for each conducting track in cable 303. Cable 303 comprises conducting tracks (not shown in FIG. 4C) to connect each of distal electrodes 132 to a designated proximal contact 322. Electrodes 132, which may include a relatively large number of electrodes, provide an array of electrodes on the distal end of probe 130. The array of electrodes may provide for fine adjustment capabilities for sensing and stimulation with lead 300.

In other examples, a DBS lead may include, for example, four 1.5 millimeters wide cylindrical electrodes, at the distal end spaced by between about 0.5 millimeters and 1.5 millimeters. In this example, a diameter of the medical lead may be about 1.27 millimeters and the metal used for the electrodes and the interconnect wires may be an alloy of platinum and iridium. The coiled interconnect wires may be insulated individually by fluoropolymer coating and protected in an 80 micron urethane tubing. With such an electrode design, the current distribution may emanate uniformly around the circumference of the electrode, which leads to stimulation of all areas surrounding the electrode.

As shown in FIG. 4C, proximal end 310 of thin film 301 arranged at proximal end 311 of DBS probe 130 is electrically connected to ALC 111 via interposer 324. For example, as will be described below, one or more individual electrical contacts (not shown in FIGS. 4B and 4C) of interposer 324 may be electrically coupled to respective contacts 322 located at proximal end 310 of thin film 301. Interposer may include another set of individual electrical contacts may be electrically coupled to respective contacts of connector 520 of ALC. Interposer 324 may include conductive tracks may running between the contacts to electrically couple the individual contacts at proximal end of thin film 301 to the electronics module 500 via connector 520 of ALC 111. In this configuration, contacts 322 of thin film 301 do not have to be located within the housing of ALC 111 in direct contact with connector 520 of ALC 111. Instead, interposer 324 may serve to electrically couple contacts 322 at distal end 310 of thin film 301 (and electrodes 132 via tracks 320) to connector 520 of ALC 111. In such a configuration, electrical signals may be conducted between electrodes 132 and ALC 111, e.g., for delivery of electrical stimulation and/or sensing of bioelectrical brain signals.

As compared to probe 130, such a design may limit fine spatial control over stimulation field distributions. The lack of fine spatial control over field distributions implies that stimulation easily spreads into adjacent structures inducing adverse side effects in about thirty percent of the patients. To overcome this problem, medical leads with high-density electrode arrangements, such as those examples illustrated herein, facilitate electrical field position adjustments in smaller increments, hence providing the ability to steer the stimulation field to the appropriate target.

The clinical benefit of DBS may be largely dependent on the spatial distribution of the stimulation field in relation to brain anatomy. To improve efficacy and efficiency of DBS while avoiding unwanted side effects, precise control over the stimulation field is important. Electrodes 132 of probe 130, with high-density electrode arrangements, provide much greater adjustability and precision than a medical lead with cylindrical electrodes.

Thin film structures may provide an advantage that small structures may be built of with this technology. A thin film is a layer or multilayer structure of material ranging from fractions of a nanometer (monolayer) to several micrometers in thickness. Electronic semiconductor devices and optical coatings may be the main applications benefiting from thin-film construction. Thin film technology and thin film manufacturing processes may allow the manufacturing of leads for medical purposes such as neurostimulation leads like, for example, DBS leads with diameters of less than 2 mm, for example 0.75 mm to 1.50 mm and a plurality of electrodes, such as 40 electrodes, although any number of electrodes may be used, including more or less than 40 electrodes (e.g., 10, 20, 30, 50 or 60 electrodes). In addition, thin film technology allows for various configurations of high density electrode arrangements, including, for example, a series of small ring electrodes or an arrangement of electrodes with more complex geometries. During stimulation or sensing, different combinations of electrodes may be used to precisely direct the stimulation or sensing within a patient.

However, thin film structures used to form the leads with high density electrode arrangements may be relatively fragile, and the handling of the leads may be difficult. Connecting thin film 301 at proximal end 310 of probe 130 to ALC 111 requires forming electrical connections between proximal contact 322 and ALC 111 as well as providing a durable mechanical connection between probe 130 and ALC 111 to facilitate a reliable electrical connection.

Figure 5:
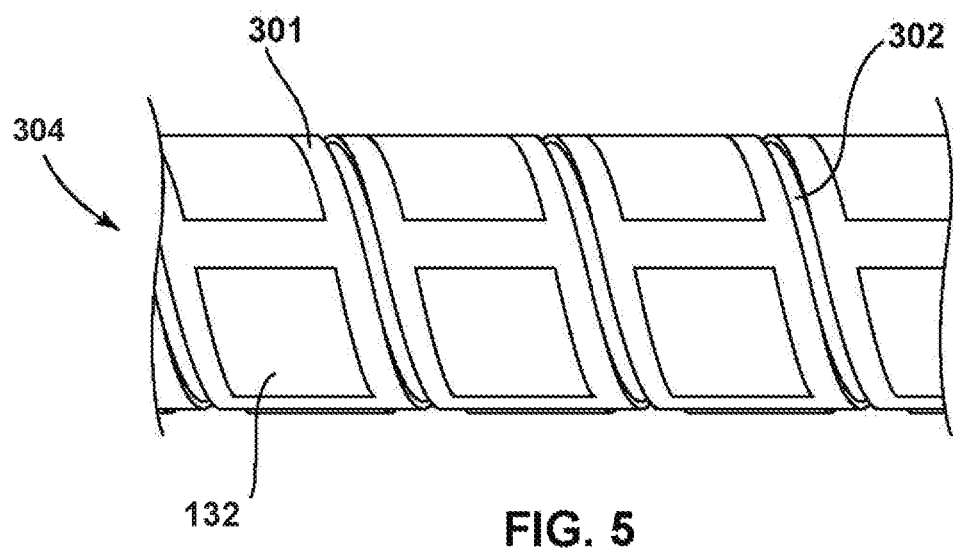
FIGS. 5-14 are conceptual diagrams illustrating various aspects of an example medical lead including a thin film wound wounds around an elongated carrier and coupled to an interposer for mechanical and/or electrical connection to an ALC.
Figure 6:
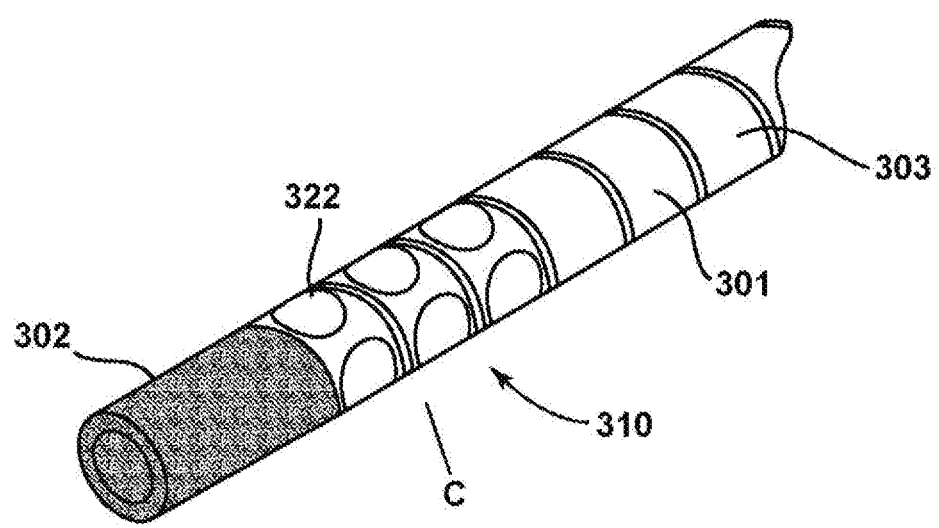

FIG. 5 is a diagram showing distal end 304 of thin film 301 wound around elongated carrier 302. Similarly, FIG. 6 is a perspective view of proximal end 310 of lead 300, which shows thin film 301 wound around elongated carrier 302. Electrodes 132 are illustrated as being rectangular in FIG. 5, although the function is the same as with the rectangular variation illustrated in FIG. 3 or other geometrical shape. Connecting portion C is located at proximal end 310 of thin film 301 and is used to connect proximal end 310 with interposer 324 and ALC 111, as described herein.

Thin film 301 may be wound around the outer surface of elongated carrier 302 using a winding tool or other suitable apparatus. With a winding tool, at first, distal end 304 of thin film 301 may be clamped to elongated carrier 302 in the correct angle. Then, the winding tool may be started and thin film 301 is wound around elongated carrier 302 with a certain pitch. The pitch may be, for example, around 1 mm. This may result in a desirable distal array of electrodes 132 for lead 300 including thin film 301 and elongated carrier 302. In addition to winding thin film 301 around elongated carrier 302 to attach thin film 301 to carrier 302, thin film 301 the lower surface of thin film may also be bonded to the outer surface of carrier 302 via an adhesive and/or an outer coating may be applied thin film 301 after being wound around carrier 302 at one or more locations of lead 300.

Thus, both ends of thin film 301, i.e., proximal end 310 and distal end 304 of thin film 301 may be wound and attached to elongated carrier 302, e.g., as compared to examples in which a portion of proximal end 301 is not wound around the outer surface of carrier 302 but instead is detached from carrier in the sense that it is not in contact with the surface of elongated carrier 302 or directly adhered to the surface of elongated carrier 302. According to one example of the present disclosure, the inner surface of thin film 301 may be completely attached to elongated carrier 302. By this attachment, the stability of the lead may be increased. Furthermore, any gaps and spaces between the thin film and the elongated carrier may be closed by the attachment. After the winding process, the complete thin film 301, i.e., proximal end 310, cable section 303 with conducting tracks 320 and distal end 304 with array of electrodes 132 is positioned on elongated carrier 302 in a spiral, helical, and/or coiled configured.

As shown in FIG. 6, interconnect contacts 322 may be exposed on the outer surface of thin film 301 at proximal end 301. Electrical contacts 322, as shown in FIG. 6, are circular but they may be also formed with a square, oval, triangular, or other suitable shape The exposed contacts 322 may allow for contacts 322, and corresponding tracks 320 and electrodes 132 of thin film, to be electrically coupled to, e.g., electrical connector 520 of ALC 111.

In some examples, to electrically connect contacts 322 of thin film 301 to electrical connector 520 of ALC 111, the proximal portion 310 of thin film 301 including contacts 322 may not be wound or otherwise attached to the surface of elongated carrier to allow that portion thin film 301 to be inserted into the housing of ALC 11 and brought into direct contact with electrical connector 520. However, thin film 301 may form a relatively weak mechanical and/or electrical connection with ALC 111 in such a configuration, e.g., due to the relatively fragile composition of thin film 301 including tracks 322, particularly when the portion of thin film 301 is not wound around carrier 302.

Figure 7:
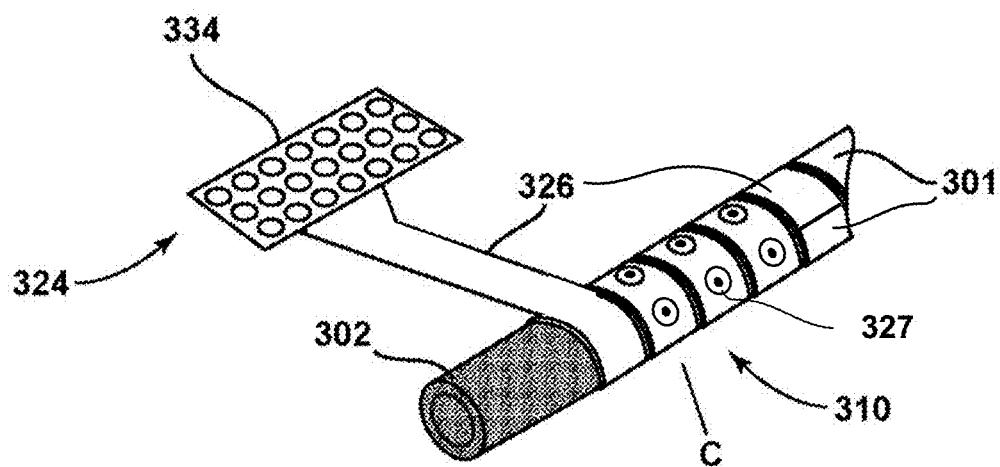
Figure 16:
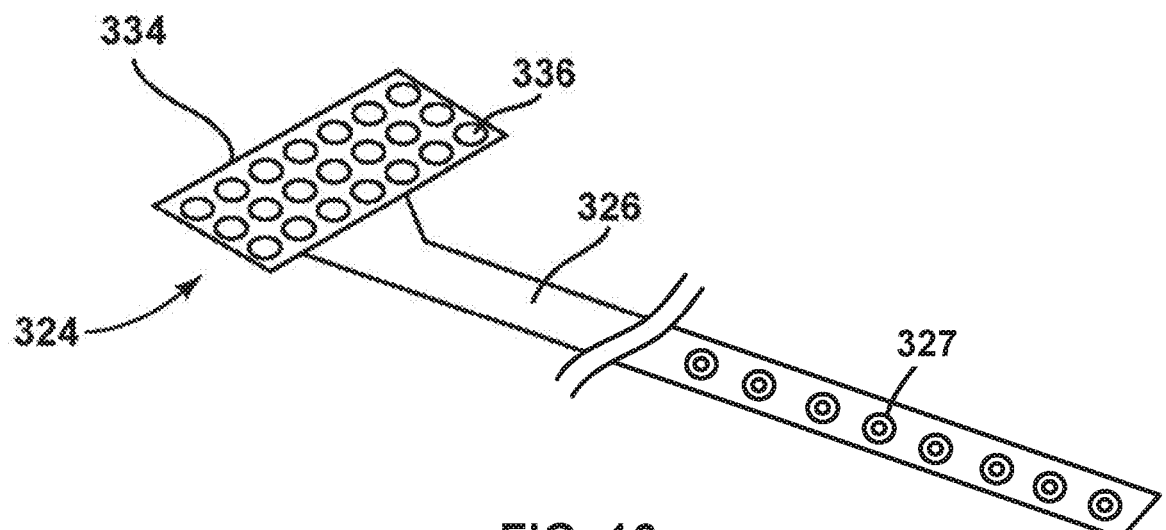
FIG. 16 is a conceptual diagram illustrating an example of an interposer for mechanically and/or electrically connecting a thin film to an ALC.

In contrast, in the example shown in FIG. 6, for example, distal end 310 of thin film 301 may be wound entirely around carrier 302 such that the portion of thin film 310 including contacts 322 is wound around carrier 302. In such an example, interposer 324 may be used as an intermediary between electrical connector 520 of ALC 111 and electrical contacts 322. For example, interposer 324 may be a separate element including strip connector 326 with electrical connector rings 327, which function as electrical contacts that mate to electrical contacts 322 of thin film 301 when electrical contacts 322 are wound around elongated carrier 302. FIG. 16 is a diagram illustrating an example configuration of interposer 324 including strip connector 326 including connector rings 327 extending through the thickness of strip connector 326 as electrical contacts (shapes other than rings may be used for the contacts). As shown in FIG. 7, strip connector 326 of interposer may be wound around carrier 302 on top of electrical contacts 322 of thin film 301. The arrangement of rings 327 on interposer 324 relative to the arrangement of contacts 322 wound around carrier 302 may be such that individual rings 327 contact individual connectors 322 to electrically couple the rings 327 to the connectors 322. The portion of interpose 324 wound around carrier 302 and thin film 301 may be attached to carrier 302 and thin film 301 via an adhesive or other suitable technique.

Figure 8:
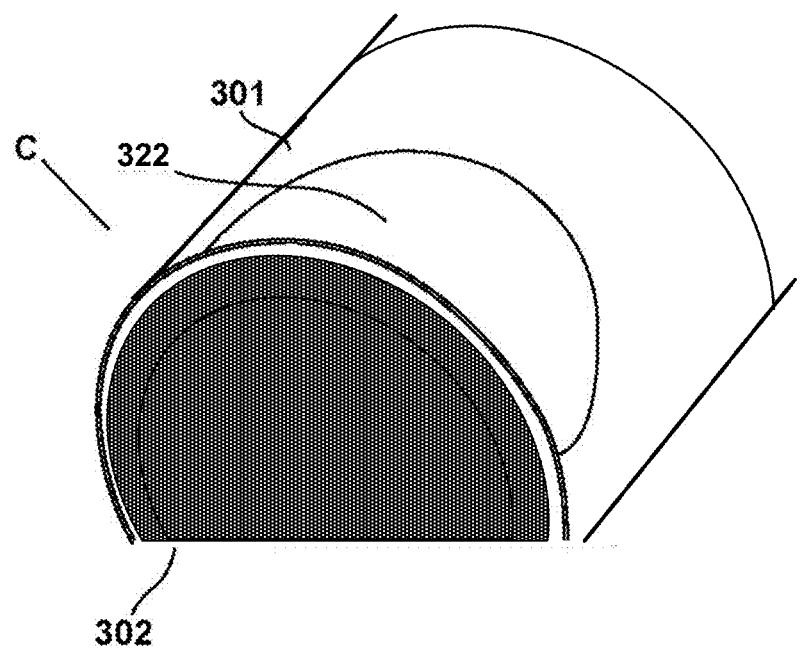
Figure 9:
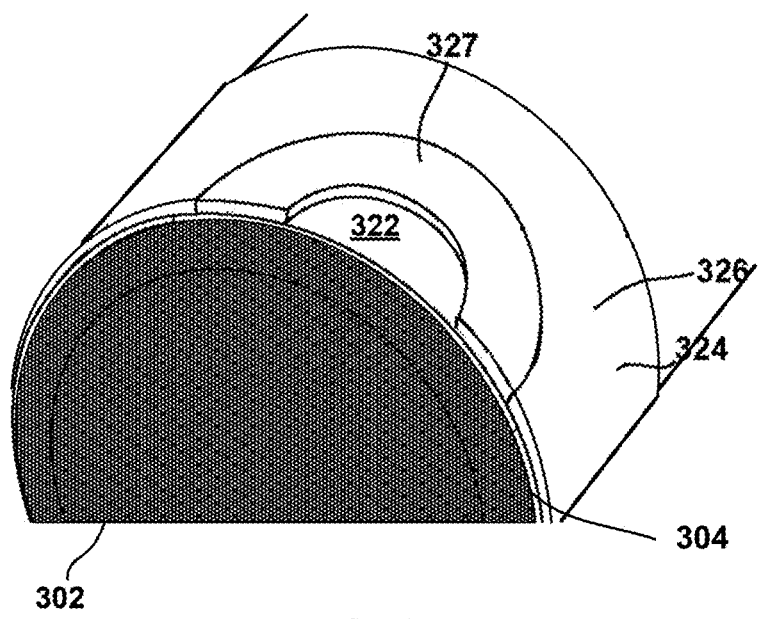
Figure 10:
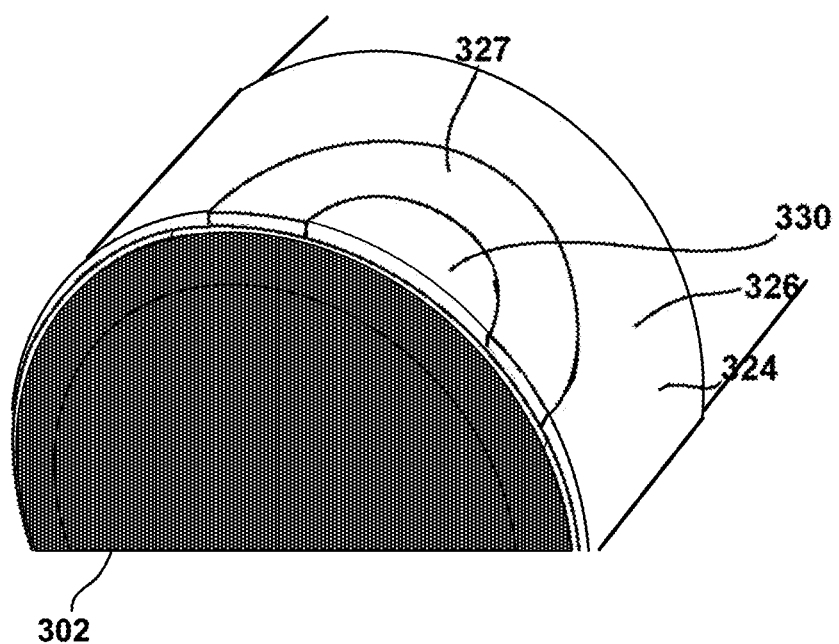

FIG. 8 is a conceptual diagram illustrating cross section of a portion of one contact 322 of thin film 301 wrapped around carrier 302. For ease of illustration, only a single contact 322 is shown. However, as described herein, thin film 301 may include multiple connectors 322 wound around carrier 302. FIG. 9 is a diagram of the same view but with strip connector 326 wound around the outside of the thin film and contact 322 such that electrical connector ring 327 is positioned over contact 322. FIG. 10 is a diagram showing the same view of FIG. 9 except that a conductive polymer adhesive 330 has been applied within the center of ring 327 to bond connector ring 327 of interpose 324 to contact 322 of thin film 301 in a manner that electrically couples ring 327 to contact 322. Any suitable technique may be used to electrically couple ring 327 to contact 322.

Figure 11:
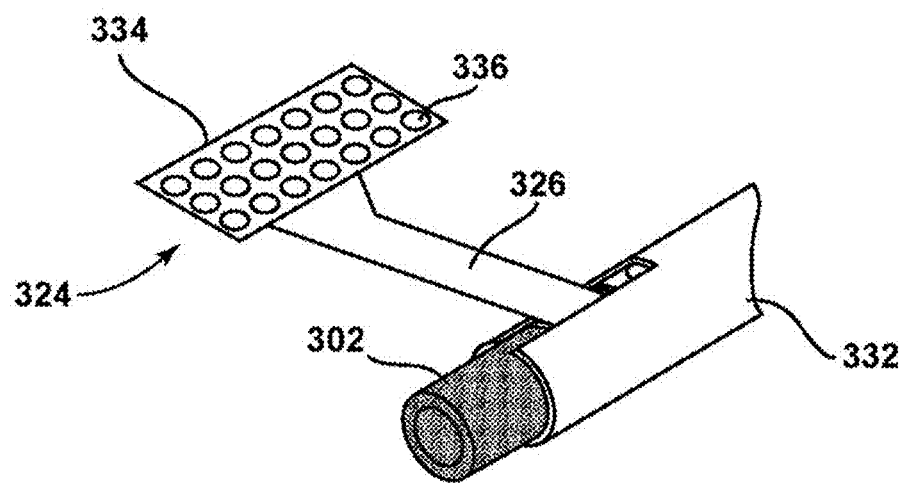
Figure 17:
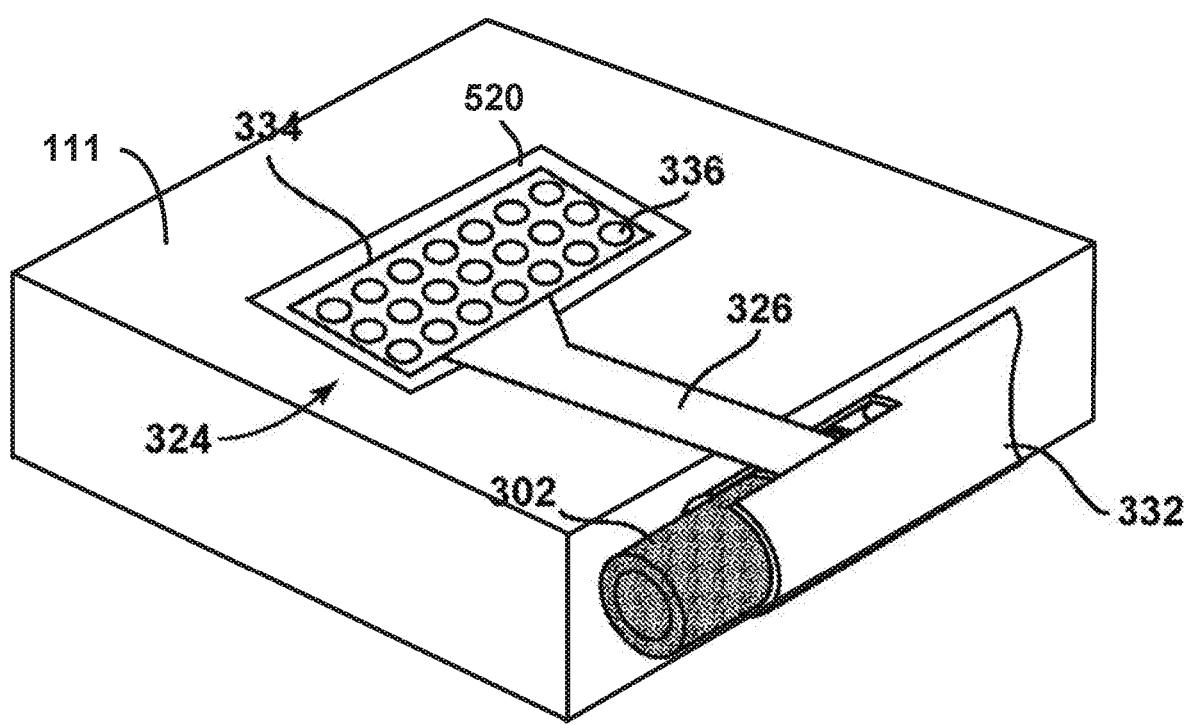
FIG. 17 is a conceptual diagram illustrating an example system including an ALC connected to an medical lead including a thin film via an interposer.

As shown in FIG. 7, e.g., interposer 324 further includes array of electrodes 334, and individual electrodes (e.g., individual electrode 336) of array 334 connect directly to respective individual connector rings 327 located on strip connector 326, e.g., via one or more conductive tracks extending within interposer 324. Array of electrodes 334 facilitate connection of contacts 322 of thin film 301 to connector 520 of ALC 111. FIG. 17 is a diagram illustrating an example configuration in which array of electrodes 334 is position over electrical connector 520 of ALC 111. The array of electrodes 334 are arrange relative to the individual connectors of electrical connector 520 of ALC 111 such that individual electrodes of array 334 electrically couple with individual connectors of connector 520. In this manner, interposer 324 may provide for electrical connection between electrical connector 520 of ALC 111 and electrical contacts 322 of thin film 301 on an individual basis despite the fact that electrical contacts 322 are wound around carrier 302. When electrically coupled in such a manner, electrical signals may be conducted from ALC 111 (and IPG 110) to electrodes 132 via interposer 324 and conductive tracks 320 of thin film. Moreover, as shown in FIG. 17, interposer 324 may mechanically couple lead 300 to ALC 111. In some examples, interpose 324 may formed from a material that exhibits greater mechanical strength that thin film (e.g., a poly imide material) and/or exhibit dimensions that provide for desirable mechanical strength to provide a better mechanical connection between lead 300 compared to thin film 301 being directly connected to ALC 111. A cover for ALC 111 may be attached after interposer has been connected to ALC 111 in the manner shown in FIG. 17 to provide for a substantially sealed housing for ALC 111. Moreover, as shown in FIGS. 11 and 17, protective sleeve 332 may be placed over interposer 324, e.g., to protect the connections between rings 327 of interposer 324 and contacts 322 of thin film 301 as well cover any exposed conductive surfaces of those connections.

Although examples of the disclosure have been described with regard to strip connector 326 of interposer 324 being wound over thin film 301 on carrier 302 to connect rings 327 to contacts 322, in other examples, strip connector 326 may first be wound onto carrier 302 and then distal end 310 of thin film 301 may be wound over strip connector 326 in a configuration that connects rings 327 to contacts 322.

Examples of the disclosure may provide for one or more advantages. In one example, an advantage is achieved in that instead of using a relatively vulnerable thin film portion for forming a mechanical and electrical connection to the connectors of, for example, ALC 111 or other driving electronics of the lead, a more stable and reliable mechanical and electrical connection may be established by attaching an interposer, as described, as well as winding the entire proximal end of thin film 301 to carrier 302. In some examples, no part of thin film 301 extends or protrudes from elongated carrier 302. De-attaching or stripping of thin film 301 from elongated carrier 302 is prevented by eliminating the extending or protruding portions that may act as stripping starting portion in the most vulnerable parts of the thin film 301. For instance, the end portions of thin film 301 may be fully supported by elongated carrier 302. In this manner, after the winding process, entire thin film 301, which is the most fragile and vulnerable part of lead 300, may be connected to elongated carrier 302. Thus, the risk of breaking thin film 301 is limited. Interposer 324 may be designed to be much stronger than thin film 301 and has a greater thickness and is less fragile. Thus, the electrical and mechanical connection between thin film 301 and the electronics within ALC 111 may be improved via the strength of interposer 324 as compared to thin film 301.

Figure 12:
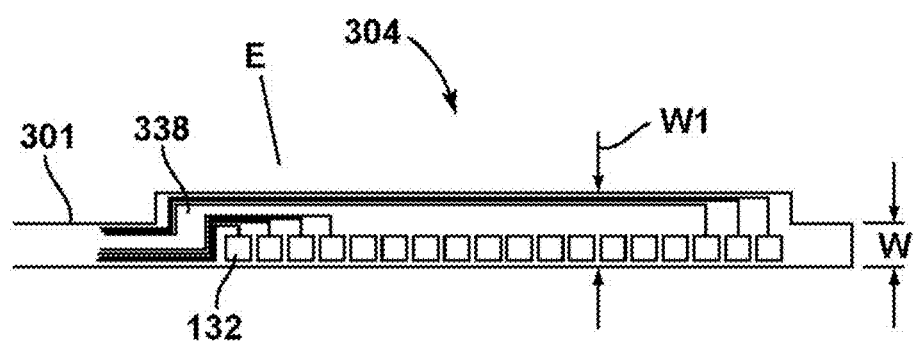
Figure 13:
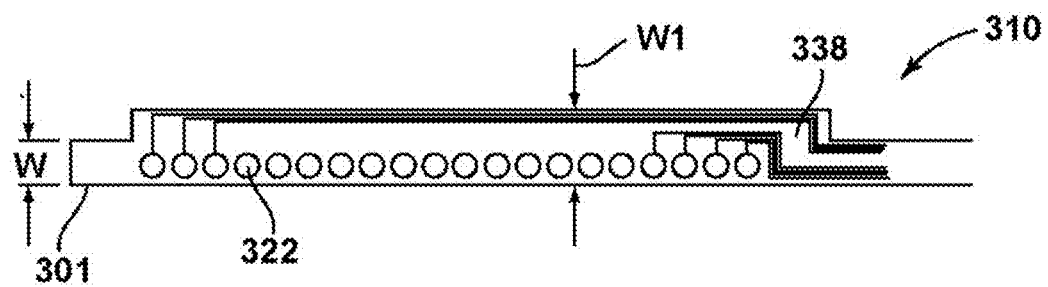
Figure 14:
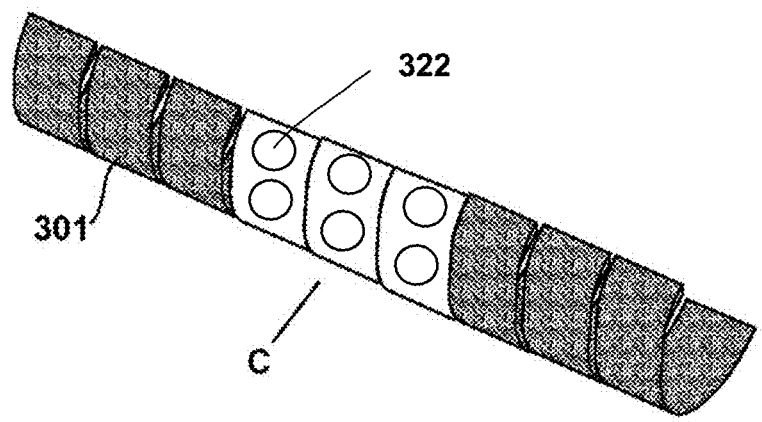

FIGS. 12-14 show a further example of lead 300 with a modified thin film design. As shown in FIG. 13, a portion of proximal end 310 of thin film 301 has an increased width W1 as opposed to adjacent sections of the thin film, such as the adjacent "cable" section having a width "w" extending between distal end 304 and proximal end 310 which carry conductive tracks 338 (also shown as tracks 322 in FIG. 4A) extending from individual electrodes 132 to individual contacts 322. For examples, the width of W1 may be at least twice the width of W in FIG. 13. Similarly, as shown in FIG. 12, the electrode array portion E of thin film 301 may have an increased width W1 as opposed to adjacent sections of the thin film, such as the adjacent "cable" section having a width "w" extending between distal end 304 and proximal end 310 which carry conductive tracks 338 (also shown as tracks 322 in FIG. 4A). Although only six individual conductive tracks 338 are shown in FIGS. 12 and 13, it is understood that number of individual conductive tracks 338 may be that same as the number of individual electrodes 132 in FIG. 12 and the same as the number of individual contacts 322 in FIG. 13. The individual conductive tracks 338 may be electrically isolated from each other in thin film 301.

By such a design, enough space is given to place connecting tracks 338 for electrical contacts 322 in the connecting portion beside and adjacent to electrical contacts 322. The same is possible for electrodes 132, where connecting tracks 338 for electrodes 132 may be placed beside and adjacent to electrodes 132. In an alternative example, a dual layer process may be used to allow the traces to run underneath the electrical contacts 322 and electrodes 132 without increasing the width W of the thin film 301. However, since the electrodes 132 and/or contacts 322 may be only slightly smaller than the width W this process may make the manufacturing process more complex, which could increase the production costs.

The design shown in FIGS. 12 and 13 does not influence the winding process. As shown in FIG. 14, connecting portion C (portion E isn't shown in FIG. 14) has an increased width and may be wound with the same pitch around the elongated carrier, with the only difference as compared to the thin film design of FIGS. 4A-10 that a part of thin film 301 is wound on top of the previously wound thin film section. In particular, as illustrated in FIG. 14, windings of connecting portion C overlap one another due to the increased width of thin film 301 at connecting portion C. However, electrical contacts 322 remain exposed. Instead, within connecting portion only portions of thin film 301 including connecting tracks 338 are covered by the subsequent winding. Portion E may be wound around carrier 302 in a similar manner.

Figure 15:
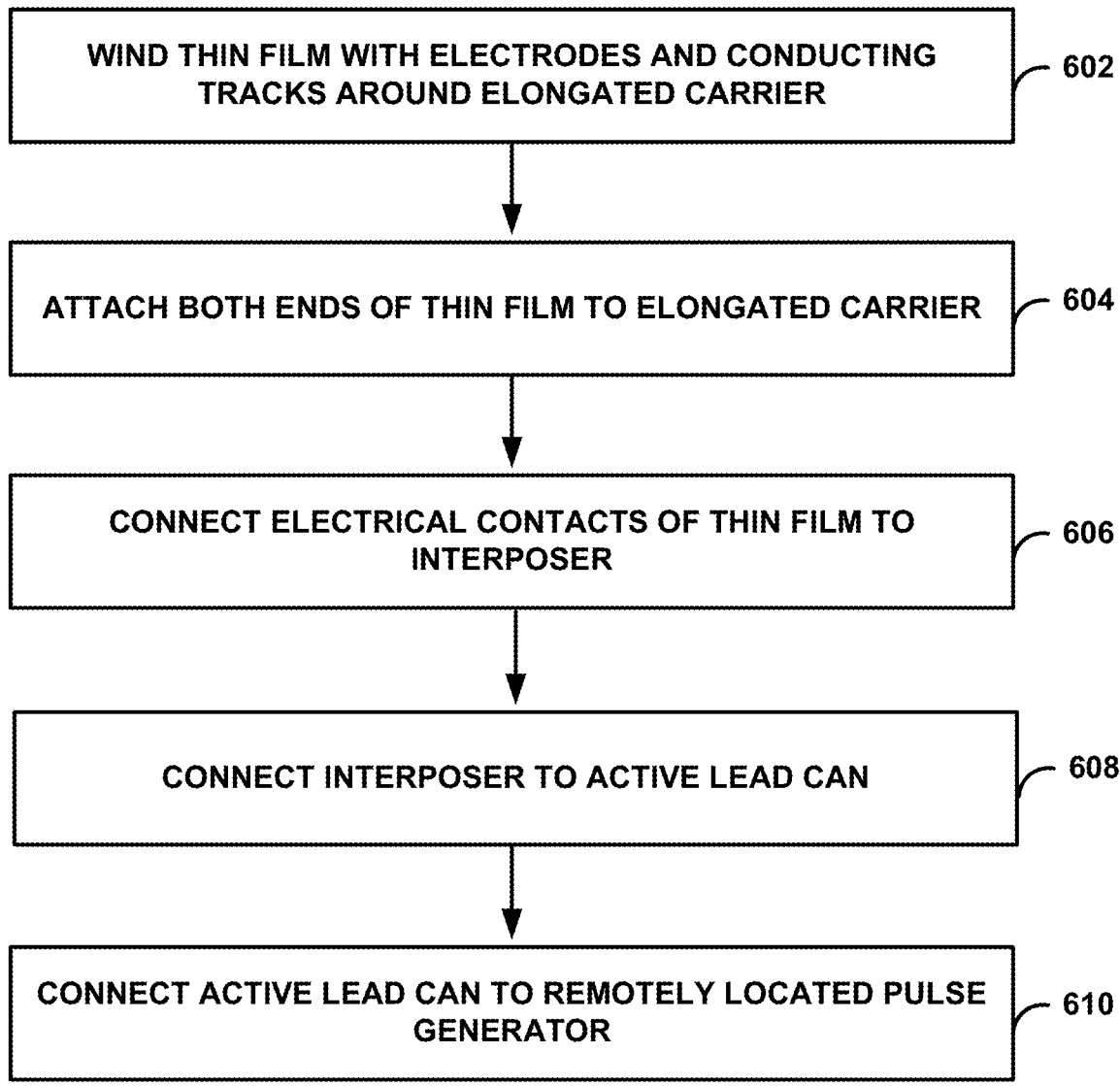
FIG. 15 is a flowchart illustrating example techniques for manufacturing a medical lead.

FIG. 15 is a flowchart illustrating example techniques for manufacturing a medical lead. For clarity, the techniques of FIG. 15 are described with respect to medical lead 300, as illustrated in FIGS. 3-14.

Thin film 301 with electrodes and conducting tracks is wound around elongated carrier 302 in a helical fashion to form probe 130 (602). Next, both proximal end 310 and distal end 304 of thin film 301 are attached to elongated carrier 302, for example, by gluing (604). Optionally, one surface of thin film 301 may be completely attached to elongated carrier 302, such as by gluing thin film 301 to elongated carrier 302 all along the length of the thin film 301.

Proximal electrical contacts 322 of thin film 301 may be connected to electrical contacts (rings 327) of interposer 324 (606). This may be done by gluing, especially be using glue droplets. Interposer 324 may be connected to ALC 111 (608), e.g., to couple electrode array 334 to electrical connector 520, and ALC 111 may be connected to IPG 110, e.g., via lead 220 and lead extension 120, to electrically connect medical probe 130 to remotely located pulse generators of IPG 110 (610).

While the techniques described herein are suitable for systems and methods involving DBS therapies, and may be used treat such disorders as Parkinson's disease, Alzheimer's disease, tremor, dystonia, depression, epilepsy, OCD, and other disorders, the techniques are not so limited. One or more such techniques and systems may be applied to treat disorders such as chronic pain disorders, urinary or fecal incontinence, sexual dysfunction, obesity, mood disorders, gastroparesis or diabetes, and may involve other types of stimulation such as spinal cord stimulation, cardiac stimulation, pelvic floor stimulation, sacral nerve stimulation, peripheral nerve stimulation, peripheral nerve field stimulation, gastric stimulation, or any other electrical stimulation therapy. In some cases, the electrical stimulation may be used for muscle stimulation.

In addition, it should be noted that examples of the systems and techniques described herein may not be limited to treatment or monitoring of a human patient. In alternative examples, example systems and techniques may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis. The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A medical device system for at least one of delivery of electrical stimulation pulses or sensing of physiological signals, the system comprising:
   an elongated carrier;
   a thin film helically wound around the elongated carrier, wherein the thin film includes a first plurality of electrical contacts, a plurality of electrodes located distal to the first plurality of electrical contacts, and a plurality of conducting tracks, each of the plurality of conducting tracks providing an electrical connection between at least one of the plurality of electrodes and one of the first plurality of electrical contacts, wherein the thin film is wound around the elongated carrier from a distal end of the thin film to a proximal end of the thin film; and
   an interposer including a second plurality of electrical contacts, wherein each contact of the second plurality of electrical contacts is electrically coupled to at least one of the first plurality of electrical contacts of the thin film, and
   wherein a distal portion of the interposer including the second plurality of electrical contacts is helically wound around a proximal portion of the elongated carrier at least one of over the first plurality of electrical contacts of the thin film or under the first plurality of electrical contacts of the thin film such that the second plurality of electrical contacts of the interposer align with the first plurality of electrical contacts of the thin film.

2. The system of claim 1, wherein no part of the thin film extends or protrudes from the elongated carrier at both a proximal end and a distal end of the elongated carrier.

3. The system of claim 1, wherein the thin film has a substantially consistent width over its length from the distal end to the proximal end of the thin film.

4. The system of claim 1, wherein the first plurality of electrical contacts are located at the proximal end of the thin film.

5. The system of claim 1, wherein the interposer comprises a third plurality of electrical contacts located proximal the second plurality of electrical contacts, wherein the third plurality of electrical contacts are configured to electrically couple the second plurality of electrical contacts to an electrical connector of an active lead can.

6. The system of claim 5, further comprising the active lead can including a switch matrix, and wherein the active lead can includes a substantially sealed housing containing the switch matrix.

7. The system of claim 6, further comprising an implantable medical device coupled to the active lead can via a lead.

8. The system of claim 7, wherein the active lead can includes a pulse generator.

9. The system of claim 7, wherein the implantable medical device includes a pulse generator.

10. The system of claim 7, wherein N electrical connection tracks are defined between the implantable medical device and the active lead can, and wherein N is less than a total number of individual electrodes of the plurality of electrodes.

11. The system of claim 1, wherein the proximal end of the thin film, including the first plurality of electrical contacts, has a greater width than portions of the thin film including the plurality of conducting tracks.

12. The system of claim 1, wherein the distal end of the thin film, including the first plurality of electrodes, has a greater width than portions of the thin film including the plurality of conducting tracks.

13. The system of claim 1, wherein the thin film and the interposer overlap with each other over multiple windings on the elongated carrier where the second plurality of electrical contacts of the interposer are electrically coupled to the first plurality of electrical contacts of the thin film.

14. The system of claim 1, wherein the interposer is a separate element from the thin film and is attached to the thin film by an adhesive.

15. The system of claim 1, wherein the interposer is helically wound over the thin film.

16. The system of claim 15, wherein each contact of the second plurality of contacts defines an aperture extending through the interposer, wherein the aperture of each contact of the second plurality of contacts is aligned over a corresponding contact of the first plurality of electrical contacts of the thin film.

17. The system of claim 16, further comprising a conductive adhesive within the aperture of each contact of the second plurality of contacts that bonds and electrically couples each contact of the second plurality of contacts to the corresponding contact of the first plurality of electrical contacts of the thin film.

18. The system of claim 1, further comprising a protective sleeve over the interposer and the thin film at the proximal portion of the elongated carrier.

19. A medical device system comprising:
an implantable medical device including a first substantially sealed housing;
an active lead can including a second substantially sealed housing operatively coupled to the implantable medical device; and
a medical lead extending from the active lead can and operatively coupled to the active lead can, wherein the medical lead includes:
an elongated carrier;
a thin film helically wound around the elongated carrier, wherein the thin film includes a first plurality of electrical contacts, a plurality of electrodes located distal to the first plurality of electrical contacts, and a plurality of conducting tracks, each of the plurality of conducting tracks providing an electrical connection between at least one of the plurality of electrodes and one of the first plurality of electrical contacts, wherein the thin film is wound around the elongated carrier from a distal end of the thin film to a proximal end of the thin film;
an interposer including a second plurality of electrical contacts, wherein each contact of the second plurality of electrical contacts is electrically coupled to at least one of the first plurality of electrical contacts of the thin film, and
wherein a distal portion of the interposer including the second plurality of electrical contacts is helically wound around a proximal portion of the elongated carrier at least one of over the first plurality of electrical contacts of the thin film or under the first plurality of electrical contacts of the thin film such that the second plurality of electrical contacts of the interposer align with the first plurality of electrical contacts of the thin film.

20. A method of manufacturing a medical device system comprising:
helically winding a thin film around an elongated carrier, wherein the thin film includes a first plurality of electrical contacts, a plurality of electrodes located distal to the first plurality of electrical contacts, and a plurality of conducting tracks, each of the plurality of conducting tracks providing an electrical connection between at least one of the plurality of electrodes and one of the first plurality of electrical contacts, and wherein the thin film is wound around the elongated carrier from a distal end of the thin film to a proximal end of the thin film; and
helically winding a distal portion of an interposer including a second plurality of electrical contacts around a proximal portion of the elongated carrier such that each contact of the second plurality of electrical contacts is electrically coupled to at least one of the first plurality of electrical contacts of the thin film, wherein the distal portion of the interposer is at least one of wound over the first plurality of electrical contacts of the thin film or wound under the first plurality of electrical contacts of the thin film such that the second plurality of electrical contacts of the interposer align with the first plurality of electrical contacts of the thin film.

21. The method of claim 20, wherein no part of the thin film extends or protrudes from the elongated carrier at both a proximal end and a distal end of the elongated carrier after being wound around the elongated carrier.

22. The method of claim 20, wherein the interposer comprises a third plurality of electrical contacts located proximal the second plurality of electrical contacts, the method further comprising electrically coupling the third plurality of electrical contacts to an electrical connector of an active lead can to provide an electrical connection between the active lead can and the plurality of electrodes of the thin film.

* * * * *